United States Patent [19]

Cho et al.

[11] 4,389,349

[45] Jun. 21, 1983

[54] PROCESS FOR PREPARING OF N-PHOSPHENOMETHYL GLYCINE

[76] Inventors: Hung H. Cho, 303-8-4-1 Sec.3, Nanking E. Rd., Taipei; Min F. Chen, No. 6, Lane 430 Sec. 1, Taichung-Kan Taichung, both of Taiwan

[21] Appl. No.: 342,723

[22] Filed: Jan. 25, 1982

[51] Int. Cl.$^3$ .............................................. C07F 9/38
[52] U.S. Cl. ............................ 260/502.5 F; 260/941; 260/970
[58] Field of Search ..................................... 260/502.5

[56] References Cited

U.S. PATENT DOCUMENTS 3,977,860  8/1976  Franz ............................... 260/502.5
4,053,505 10/1977  Dutra ................................. 269/970

FOREIGN PATENT DOCUMENTS 2528633  2/1976  Fed. Rep. of Germany ... 260/502.5

Primary Examiner—Joseph E. Evans
Attorney, Agent, or Firm—Darby & Darby

[57] ABSTRACT

Process for producing N-phosphenomethyl glycine, comprising reacting alkyl glycinate hydrochloride with paraformaldehyde to produce alkyl glycinate methylene chloride, said alkyl glycinate methylene chloride being reacted with phosphite to produce dialkyl phosphenomethyl alkyl glycinate, and finally converted to N-phosphenomethyl glycinate.

10 Claims, No Drawings

PROCESS FOR PREPARING OF N-PHOSPHENOMETHYL GLYCINE

This invention relates to a process for producing N-phosphenomethyl glycine. N-phosphenomethyl glycine is a useful herbicide. The well-known processes for preparing the compound are, for example, to react iminodiacetic acid with phosphite such as diphenyl phosphite or dialkyl phosphite, and then oxidize with a strong acid or other oxidizing agent or by electrolysis. Due to the complexities of reaction process, and since the decomposition is carried out at elevated temperature in the presence of strong acid and other oxidizing agents, products will be contaminated with a large amount of by-produced impurities and in the meantime will cause polymerization due to the action of strong acids, so the yield is low and further purification by use of recrystallization is needed.

In consideration of these drawbacks, the present inventor has conducted intensive studies together with experimental reviews and finally completed the present invention.

The primary objective of the present invention is to simplify the process for preparing N-phosphenomethyl glycine and to obtain N-phosphenomethyl glycine at a high purity and high yield.

Therefore, the novel process for preparing said N-phosphenomcthyl glycine according to the present invention is characterized by replacing the previously used iminodiacetic acid with glycine ester.

The reason iminodiacetic acid has been used in the prior art is due to the fact that, in $-NH_2$ of glycine, two atoms of hydrogen will react with dialkyl phosphite, and there is a great chance to form N-di(phosphenomethyl) glycine, rather than formation of N-phosphenomethyl glycine. In order to avoid this, in the prior art, iminodiacetic acid wherein one atom of hydrogen in the $-NH_2$ of glycine being blocked has been used. However, the disadvantage of said process is as previously mentioned, the process itself is rather complex and moreover needs decomposition by strong acids.

In order to remove these drawbacks, the present inventor has considered to use glycine directly during the course of idea gathering and research, but due to the fact that glycine is insoluble in general organic solvents glycine ester was finally chosen. Furthermore, after consideration of its stability, alkyl glycinate hydrochloride was chosen as starting material. For example, the solutility of ethyl glycinate hydrochloride in ethyl alcohol is shown as follows: (in methyl alcohol is about the same)

22° C.: 5.5% w/w
60° C.: 71.0% w/w i.e., by use of methanol or ethanol with ethyl glycinate hydrochloride dissolving therein, it should be possible to make phosphite to react with one hydrogen atom in $-NH_2$ of glycine, and therefore to synthesize N-phosphenomethyl glycine in a simple way.

In order to achieve the above objective, the present inventor has given up the prior process which starts from phosphite by chloromethylation or by reaction of mixing phosphite, formalin or paraformaldelyde, together with iminodiacetic acid, while ethyl glycinate hydrochloride first reacts with paraformaldehyde to synthesize ethyl glycinate metylene chloride, in this way it should be able to react with phosphite in the presence of acid absorber and readily obtained the objective product N-phosphenomethyl glycine. Based on this idea, the present inventor has conducted intensive studies and finally brought the present invention to the stage of industrial application. The present invention is hereinafter described as follows:

As aforementioned, although ethyl glycinate hydrochloride is hardly dissolved in acid ethanol (or methanol), its solubility is substantially increased at above 60° C. Add paraformaldehyde to hot alcoholic solution of ethyl glycinate and mix together, chloromethylation is carried out and form ethyl glycinate methylene chloride, at this point, water formed during the reaction has to be removed, this can be done by direct distillation, that is, let alcohol and water in the system constitute azeotrope of binary system and remove them simultaneously at azeotropical point, or by addition of benzene to constitute azeotrope of three-component system for the ease of water removal. The reaction liquid is always maintained under anhydrous state, therefore, approximately theoretical yield is obtained. Reaction is shown as following equation.

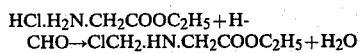

$HCl.H_2N.CH_2COOC_2H_5 + HCHO \rightarrow ClCH_2.HN.CH_2COOC_2H_5 + H_2O$

Until the above reaction completed and assured there is no any moisture remained in the reaction liquid, dropped dialkyl phosphite or diphenyl phosphite, and at the same time, dropped triethyl amine, isopropyl amine, pyridine, dialkyl aniline and the like as acid absorbers, stirred at 60° to 80° C. until a precipitate formed, precipitate removed by filtration to facilitate the filtrate for distillation, so N-dialkyl phosphenomethyl alkyl glycinate is obtained at a yield of almost over 90%.

Then, 40% of sodium hydroxide solution is added to maintain PH less than 11.5, continued to stir under 60° to 80° C. So reaction as shown in the following equation is occurred, and formed N-disodium phosphenomethyl sodium glycinate.

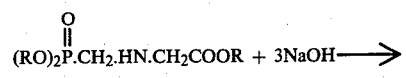

$$(RO)_2\overset{O}{\overset{\|}{P}}.CH_2.HN.CH_2COOR + 3NaOH \longrightarrow$$

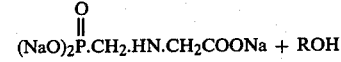

$$(NaO)_2\overset{O}{\overset{\|}{P}}.CH_2.HN.CH_2COONa + ROH$$

Finally, added acid to this reaction liquid, adjusted PH at about 1.5 to about 2.2, cooled at temperature of below 10° C., a transparent crystal is crystallized overnight, filtered and recovered to obtain N-phosphenomethyl glycinate.

The above reaction, if separate with respect to each step, is shown as follows.

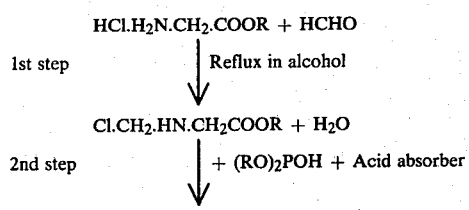

1st step: $HCl.H_2N.CH_2.COOR + HCHO$
Reflux in alcohol

2nd step: $ClCH_2.HN.CH_2COOR + H_2O$
$+ (RO)_2POH +$ Acid absorber

3rd step $$(RO)_2\overset{\overset{O}{\|}}{P}.CH_2.HN.CH_2.COOR$$

↓ + 40% NaOH Solution $$(NaO)_2\overset{\overset{O}{\|}}{P}.CH_2NH.CH_2.COONa$$

4th step  ↓ + inorganic acid $$(HO)_2\overset{\overset{O}{\|}}{P}.CH_2.HN.CH_2COOH$$

Reaction between alkyl glycinate hydrochloride and paraformaldehyde at first step proceeded by use of hydrochloric acid as depolymerization agent of paraformaldehyde trimer. This reaction proceeded readily. It can be done by distillation under reflux temperature to remove moisture with alcohol. Alternately, by addition of benzene, so as to form azeotropic moisture of a three-component system consisting of water, benzene and alcohol. Under azeotropic temperature, water will be readily removed from system.

Further, alkyl glycinate will present as hydrochloride thereof in the presence of hydrochloric acid. Under this circumstance, it is impossible to cause polymerization so reaction yield is high.

At this point, whether two hydrogen atoms in the —$NH_2$ of glycine will be completely methylated as paraformaldehyde is used in excess became widely concerned. The problem however is avoided due to the presence of alcohol.

As a matter of fact, the excess amount of paraformaldehyde will convert to formaldehyde and be distilled off together with alcohol. It will not react with secondary hydrogen in —$NH_2$. This can be confirmed from the experimental results.

Confirmation of purity of the reactant is calculated by comparison between liquid chromatography analysis and standard sample.

After completion of reaction, solvent is not necessary to be partly or totally distilled off. Dialkyl phosphite or diphenyl phosphite is added therein to carry on the second step reaction.

Second step reaction is to use dialkyl phosphite or diphenyl phosphite to react with ethyl glycinate methylene chloride obtained from first step reaction. This reaction is not necessarily performed at high temperature. If acid absorber is added into reaction liquid, it can be carried out at ambient temperature. Alternately, reaction is first carried out at ambient temperature for some time, and then raised to a higher temperature. The reaction may be started at high temperature, but the prerequisite is the use of acid absorber. As shown in the below equation, hydrochloric acid is formed during the reaction.

$$(RO)_2POH + Cl.CH_2.HN_2COOR \longrightarrow$$

$$(RO)_2\overset{\overset{O}{\|}}{P}—CH_2NH.CH_2.COOR$$
$$HCl$$

(R: alkyl or phenyl)

As aforementioned, an organic amine is preferably used as acid absorber. However, if inorganic acid absorber is used, potassium carbonate, potassium hydrogen carbonate, sodium carbonate and sodium hydrogen carbonate are prefered. If potassium hydroxide or sodium hydroxide is used, it will destroy one side of the organophorsphorous compared and one side of glycinate as well. Additionally, it is possible to use alkoxy-sodium with sodium incorporated in the alcohol, such as, methoxy-sodium or ethoxy-sodium and the like. As to the reaction temperature, either ambient temperature or elevated temperature is suitable. However, if temperature is too high, it will cause side-reactions, so ambient temperature or nearly to it is preferred.

Form the above reactions, we do not worry whether two molecule of $(RO)_2POH$ will react with glycinate to form $$\begin{array}{c} (RO)_2\overset{\overset{O}{\|}}{P}—CH_2 \\ \phantom{(RO)_2P—CH_2}\diagdown \\ \phantom{(RO)_2P—CH_2xx}N—CH_2COOR. \\ \phantom{(RO)_2P—CH_2}\diagup \\ (RO)_2\underset{\underset{O}{\|}}{P}—CH_2 \end{array}$$

Even if $(RO)_2POH$ is added in excess, it will not react with NH in $ClCH_2HN.CH_2COOR$.

Third step reaction is to use NaOH to dissolve dialkyl phosphenomethyl glycinate or diphenyl phosphenomethyl glycinate formed from the above reaction to convert to sodium salts. Rate of NaOH addition is of great importance. If NaOH is added too fast, it will cause locally vigorous reaction and cause undesired dissolution. Finally, it will cause formation of HCl. So, HCl has to be added slowly to maintain PH value no more than 11.5. Under such a strict control, only the alkyl group will be replaced so as not to destroy —NH group.

This reaction can be carried out in alcoholic solution or in water. However, from the viewpoint of economic consideration, it is preferably carried out in water.

Further, since the reaction hardly take place at ambient temperature and also —NH group is readily dissolved at elevated temperature, the temperature is preferably maintained at 60°–100° C., most preferably in the range of between 60° to 80° C. If temperature is below 60° C., the time required for this reaction will be inadequately long, while above 100° C., it will cause undesired dissolution. Reaction temperature is preferably at a range of 60° to 100° C., most preferably at a range of 60° to 80° C.

Acid decomposition of fourth step reaction is carried out by addition of NaOH at elevated temperature followed by addition of acid. Alternately, acid can be added after cooling.

Acid decomposition in prior art process is carried out by addition of a strong acid to dialkyl phosphenomethyl glycine or diphenyl phosphenomethyl glycine and/or dialkyl phosphenomethyl diacetic acid or diphenyl phosphenomethyl diacetic acid and the like, reacted at elevated temperature for a long time, so the undesirable decomposition will occur. Therefore, a tremendous amount of impurities will be present in the final reaction product. The purity of crude crystal in the first run will hardly be as high as 90%.

According to the present invention, strong acid will not be used to force decomposition as used in prior art process. In the present invention, NaOH is first added to form a sodium salt, decomposition product is then neutralized to adjust PH value, so desired product is readily crystallized out.

Therefore, the present objective will be even at ambient temperature. Therefore, side-reaction and polymerization will not occur.

Desired product N-phosphenomethyl glycine is preferably crystallized at PH of 1.5 to 2.2.

In addition, because N-phosphenomethyl glycine contains a —NH— group, it will form an acid salt if PH is less than 1.5, while a portion of N-phosphenomethyl glycine will react with NaOH to form a sodium salt if PH is higher than 2.2. Both constitute the main reason of lowering the yield.

Furthermore, because the solubility of N-phosphenomethyl glycine in water is very small, almost nonexistent, in order to achieve better crystallization, it is preferable to store overnight at a temperature below 10° C.

In the aforementioned reaction, general formula of the required dialkyl phosphite or diphenyl phosphite are shown as follows. In these formula,
1. dialkyl phosphite (RO)$_2$POH
2. diphenyl phosphite

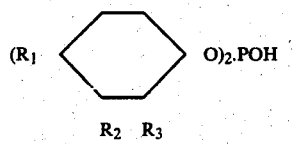

R is dialkyl phosphite may represent a $C_1$–$C_4$ alkyl, while $R_1$, $R_2$ and $R_3$ in diphenyl phosphite may represent hydrogen atom, $C_1$–$C_4$ alkyl, $C_1$–$C_4$ oxyalkyl or halogen respectively.

Furthermore, general formula of alkyl glycinate hydrochloride is shown as follows.

Wherein R may represent a $C_1$–$C_4$ alkyl group.

The invention is illustrated by the following Examples. By way of these Examples, the aforementioned objectives, processes, characteristics and other advantages will be further understood.

EXAMPLE 1

70 g of 98.5% ethyl glycinate hydrochloride is added to a 500 cc four-neck a, 280 cc of ethanol and 140 cc of benzene are then added, stirred with magnetic stirrer, finally, 16 g of paraformaldehye (98% purity) is added separately in four times. When temperature elevated to above 55°–60° C. The whole mixture became transparent. After refluxing at 75° C. for 30 minutes, cooler is inclined to distil azeotropic mixture of three-component system consisting of ethanol, benzene and water. After about four hours, use moisture detector to analyze moisture content in the distillate, until total moisture in the distillate reaches more than 8.5 g. Continue distillation to have benzene completely distilled out. Then, 91 g of diethyl phosphite is dropped through a funnel, meanwhile, 65 g of dimethyl aniline is dropped at a rate equivalent to two-thirds that of diethyl phosphite. Brought temperature to about 65°–70° C. and stirred. After addition of total amount of diethyl phosphite and dimethyl aniline is completed, continued to heat and stirred for 2–3 hr, then determined with liquid chromatography. End point of reaction is reached if peak of ethyl glycinate methylene chloride appeared in gas chromatography has been dispersed. Reaction liquid is cooled, precipitated and filtered. Filtrate is washed several times with methanol, washing solution and filtrate, are combined then methanol is recovered by distillation. 100 cc of water and 40% NaOH solution are added to residue. Heated for 4 hours at 70°–80° C. PH is maintained below 11.5. If PH dropped below 11.5 during heating process, NaOH has to be added again to bring up to 11.5. Cold hydrochloric acid is then added to adjust PH to 2 and stored overnight, a crystal is obtained, then cooled at a temperature of below 10° C. for 12 hours. By filtration, a crystal is again obtained, then washed with cold water three times to obtain a pure white crystal. Dry at 60° C., it weighed 76.5 g. It is analyzed by Shimazu UV-200 (sodium light) and compared with standard sample. As a result, 93% purity of product is N-phosphenomethyl glycine. Yield is about 83%, based on ethyl glycinate.

EXAMPLE 2

35 g of 98.5% ethyl glycinate hydrochloride and 200 cc of anhydrous methanol are added to a 500 cc four-neck flask, heated and stirred, then 8 g of paraformaldehyde (98% purity) are added separately in four times. After refluxing at 65° C. for 30 minutes, cooler is inclined to distil methanol while the reaction was still being carried out. At this point, moisture produced from the reaction would form an azeotropic mixture of two-component system with methanol, and distil out with methanol. Distillate is analyzed by a digital moisture detector, reaction is continued until total moisture content in distillate reached more than 4.2 g; methanol in four-neck flask should be constantly made up to maintain at a level of no less than 150 cc.

Then, 42 g of 99% diphenyl phosphite is added through a funnel, meanwhile, 21 g of pyridine is added at a rate equivalent to one half that of diphenyl phosphite. After addition is completed, refluxed at 65° C. for further 4 hours, cooled and filtered, then, crystal of pyridine hydrochloride is washed three times with methanol. Combined washing solution with filtrate, distilled again. 50 cc of water is added to the residue, washed with 40% NaOH solution to maintain PH at about 11.0–11.5 while stirred with heating at 80° C. for three hours. If PH is dropped to below 11.0 while heating period, NaOH has to be added to bring PH back to about 11.0–11.5. Then, mixture is cooled, and sulfuric acid is added to adjust PH value to about 1.5, stored overnight to obtain a crystal. The mixture is maintained at below 10° C. for a further 24 hours. Crystals are filtered, washed three times with cold water, dried at 60° C. to obtain white crystals. Yield is 37.4 g. Determined with Shimazu UV-200 (sodium light) according to method of Example 1, purity is 95.0% while yield is about 83.1%, based on ethyl glycinate.

EXAMPLE 3

63 g of 98.5% methyl glycinate hydrochloride, 250 cc of ethanol and 100 cc of benzene are added to a 500 cc four-neck flask, 17 g of 98% paraformaldehyde is added separately in four times. The reaction mixture is then stirred and heated at 75° C., refluxed for about one hour, until completely dissolved and became transparent. Cooler is inclined to distil off azeotropic mixture of a three-component system consisting of ethanol, benzene and water. Determined the moisture content in distillate by a digital moisture detector, until total moisture content in distillate reached more than 8.5 g. Continued to distil off benzene from reaction liquid while ethanol is constantly added to maintain at a level of about 200 cc.

195 g of di(p-methoxy phenyl) phosphite (98% purity) is then added dropwise, 55 g of anhydrous potassium carbonate is also added separately in four times. Temperature is always maintained at about 70° C.

After addition is completed, further refluxed for two hours, then cooled and filtered. Residue is washed three times with ethanol. Combined washing solution and filtrate, and distilled. Then, 50 cc of water is added to distillation residue, leteron 40% NaOH solution is added slowly to maintain PH value at a range from 11.0 to 11.5. The mixture is further heated and stirred at 80° C. for four hours. After cooling, concentrated hydrochloric acid is added to adjust PH value to about 1.5, a crystal is formed after stored overnight. Crystal is filtered and washed three times with cold water to obtain a white crystal. Dried at 60° C., it weighed 74.2 g. Determined by Shimazu UV-200 (sodium light) and compared with standard sample, purity of product is found to be 94.2%, and yield is about 82.9%, based on ethyl glycinate.

EXAMPLE 4

35 g of 98% ethyl glycinate hydrochloride and 150 cc of anhydrous ethanol are added to a 500 cc four-neck flask equipped with reflux cooler, thermometer and funnel. The reaction mixture is stirred and heated at 60° C. After dissolution is completed and became transparent, paraformaldehyde is added separately in four times. After paraformaldehyde is completely dissolved, the mixture is refluxed at 80° C. for 30 minutes. Then cooler is inclined to distil off the azeotropic mixture of two-component system consisting of water and ethanol. Determined the moisture content in distillate by a moisture detector. Reaction is stopped when total moisture content in distillate reached more than 4.2 g. Then, 35 g of di-(m-methyl phenyl) phosphite is added dropwise, while 27 g of triethylamine is dropped at a rate equivalent to about one-half that of di-(m-methyl phenyl) phosphite. After addition is completed, the mixture is further refluxed at 80° C. for four hours, then cooled and filtered. Precipitate is washed three times with anhydrous ethanol. Combined washing solution and filtrate, and distilled. 50 cc of water is added to distillation residue, and 40% NaOH solution is added to adjust PH value at a range from 11.0 to 11.5, while further heated 80° C. for four hours. Hydrochloric acid is then added to adjust PH value to about 2.0. Crystal is formed after stored overnight. Precipitate is filtered, washed with cold water, and dried to obtain a white crystal. Determined by Shimazu UV-200 (sodium light) and compared with standard sample, the purity of product is found to be 94.3%. Yield is 40.2 and 89.7% based on ethyl glycinate.

EXAMPLE 5

40 g of diethyl phosphite and 14.5 g of sodium methoxide are dissolved into 100 cc of methanol as a first solution.

As a second solution, it used the reaction product of ethyl glycinate hydrochloride and paraformaldehyde as obtained from the method described in Example 2, i.e., ethyl glycinate methylene chloride solution.

The aforementioned second solution is added slowly into the aforementioned first solution. After addition is completed, the mixture is continuously heated for three hours. The reaction is shown as follows:

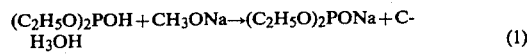

$(C_2H_5O)_2POH + CH_3ONa \rightarrow (C_2H_5O)_2PONa + CH_3OH$ (1)

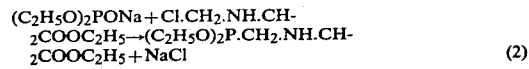

$(C_2H_5O)_2PONa + Cl.CH_2.NH.CH_2COOC_2H_5 \rightarrow (C_2H_5O)_2P.CH_2.NH.CH_2COOC_2H_5 + NaCl$ (2)

Salt formed from the reaction is filtered, and filtrate is distilled. 50 cc of water is added to residue, and 40% NaOH solution is added to adjust PH value at about 11.0 to 11.5, while further heated at 80° C. for four hours. Then, concentrated hydrochloric acid is added to adjust PH value to about 1.5. After stored overnight, filtered to remove crystal. Crystal is then washed with cold water, and dried to obtain 38.0 g of a white crystal. Purity of product is 92.5%. Yield is 83.2%, based on ethyl glycinate.

As shown in Examples described above, the present invention can simplify the process for producing N-phosphenomethyl glycine. Furthermore, the purity of product is significantly improved to enable commercial applications. The Examples shown above are only several representative reaction processes. The details thereof are not to be construed as limitations of the present invention, i.e., all substitute processes similar to processes and characteristics as indicated in the following claims shall be included in the scope of present invention.

What is claimed is:

1. A process for producing N-phosphenomethyl glycine comprising:
   (a) Reacting an alkyl glycinate hydrochloride in an alcoholic solution with paraformaldehyde in the presence of hydrogen chloride, while removing water from the reaction system, to produce alkyl glycinate methylene chloride;
   (b) Reacting said alkyl glycinate methylene chloride with a compound of the formula $X_2P_2POH$, wherein X represents a phenoxy or $C_1$–$C_4$ alcoxy radical, under anhydrous conditions and in the presence of an acid absorber to form a di-substituted phosphenomethyl alkyl glycinate and a chloride salt which is removed;
   (c) Saponifying said di-substituted phosphenomethyl alkyl glycinate at elevated temperature with sodium hydroxide to form a sodium salt thereof; and
   (d) acidifying said salt to form N-phosphenomethyl glycine.

2. The process of claim 1, wherein said alkyl glycinate hydrochloride is first dissolved in a lower alcohol solution or a mixture of a lower alcohol solution and benzene, and then reacted with paraformaldehyde in refluxing alcohol, said water removal being effected by azeotropic distillation.

3. The process of claim 2 wherein said step (a) is carried out at a temperature ranging between 60° C. and 90° C.

4. The process of claim 1, wherein said step (b) is carried out at a temperature ranging between 60° C. and 80° C.

5. The process of claim 4, wherein said acid absorber is an organic amine.

6. The process of claim 5, wherein said acid absorber is a member selected from the group consisting of triethylamine, isopropylamine, pyridine, dialkyl aniline.

7. The process of claim 1, wherein said acid absorber is an inorganic acid absorber selected from the group consisting of potassium carbonate, potassium hydrogen carbonate, sodium carbonate and sodium hydrogen carbonate.

8. The process of claim 6 or 7, wherein said di-substituted phosphenomethyl alkyl glycinate is recovered from the reaction mixture after completion of the step (b) reaction by filtering said mixture and distilling off the solvent from the filtrate.

9. The process of claim 1, wherein said saponification is carried out at a pH below 11.5, said pH having been set prior to elevating said temperature.

10. The process of claim 1 wherein during said acidification the pH is controlled to range between 1.5 and 2 the mixture being subsequently cooled to obtain N-phosphenomethyl glycine.

* * * * *